United States Patent
Bühring et al.

(10) Patent No.: US 6,913,894 B2
(45) Date of Patent: Jul. 5, 2005

(54) ANTIBODIES DIRECTED AGAINST SIGNAL REGULATOR PROTEINS

(75) Inventors: Hans-Jörg Bühring, Tübingen (DE); Axel Ullrich, München (DE); Zhengjun Chen, Germering (DE); Charles Cant, München (DE)

(73) Assignee: Eberhard-Karls-Universitat Tubingen Universitatsklinikum, Tubingen (DE)

( * ) Notice: Subject to any disclaimer, the term of this patent is extended or adjusted under 35 U.S.C. 154(b) by 42 days.

(21) Appl. No.: 10/158,415

(22) Filed: May 29, 2002

(65) Prior Publication Data

US 2003/0054415 A1 Mar. 20, 2003

Related U.S. Application Data

(63) Continuation of application No. PCT/EP00/11322, filed on Nov. 16, 2000, now abandoned.

(30) Foreign Application Priority Data

Nov. 30, 1999 (DE) .......................................... 199 57 665
Mar. 3, 2000 (DE) .......................................... 100 10 616

(51) Int. Cl.[7] .......................... C07K 16/28; C12P 21/08; G01N 33/543; G01N 33/567; G01N 33/577
(52) U.S. Cl. ................... 435/7.21; 435/70.21; 435/452; 435/332; 435/334; 436/501; 436/518; 436/548; 530/388.2; 530/388.22
(58) Field of Search .................... 435/2, 7.21, 70.21, 435/452, 332, 334; 436/501, 518, 526, 548; 530/388.2, 388.22, 391.1, 391.5, 413; 424/141.1, 143.1, 153.1, 183.1

(56) References Cited

FOREIGN PATENT DOCUMENTS

| WO | WO 97/48723 | 12/1997 |
| WO | WO 99/40940 | 8/1999 |
| WO | WO 00/66159 | 11/2000 |

OTHER PUBLICATIONS

Adams, S., et al. ( 1998) Signal–Regulatory Protein Is Selectively Expressed by Myeloid and Neuronal Cells. J. Immunol. 161:1853–1859.

Dietrich, J., et al. (2000) Cutting Edge: Signal–Regulatory Protein β1 Is a DAP12–Associated Activating Receptor Expressed in Myeloid Cells. J. Immunol. 164:9–12.

Kharitonenkov, A., et al. (1997) A Family of Proteins That Inhibit Signalling Through Tyrosine Kinase Receptors. Nature 386(13):181–186.

Seiffert, M., et al. (1998) Expression and Function of SIRPα1 and its Extracellular Ligand on Hematopoietic Cells. (Abstract) Blood 92(10): Suppl. 1, Part 1–2: 160B.

Seiffert, M., et al. (1999) Human Signal–Regulatory Protein Is Expressed on Normal, But Not on Subsets of Leukemic Myeloid Cells and Mediates Cellular Adhesion Involving Its Counterreceptor CD47. Blood 94(11):3633–3643.

Seiffert, M., et al. (1999) Molecular Characterization of SIRPα–CD47 Interactions on Hematopoietic Cells. (Abstract) Blood 94(10): Suppl 1, Part 1:47A.

Seiffert, M., et al. (2000) Expression and Function of Signal–Regulatory Proteins (SIRPs): SIRPα but not SIRPβ is Expressed on Hematopoietic Stem Cells and Interacts with CD47. Tissue Antigens 55(Suppl 1):70–71.

*Primary Examiner*—Christopher L. Chin
*Assistant Examiner*—James L. Grun
(74) *Attorney, Agent, or Firm*—Knobbe, Martens, Olson & Bear, LLP

(57) ABSTRACT

Monoclonal antibodies which bind specifically to the extracellular domain of the SIRP cell surface glycoproteins, and which, in some cases, block the interaction of SIRP with the surface molecule CD47, are described.

4 Claims, No Drawings

ANTIBODIES DIRECTED AGAINST SIGNAL REGULATOR PROTEINS

RELATED APPLICATION

This application is a continuation application of International Patent Application PCT/EP00/11322, published as WO 01/40307, in which the United States is a designated country, with an international filing date of Nov. 16, 2000, published in German under PCT Article 21(2) and now abandoned, which claims priority to a German Application 19957665.3 filed Nov. 30, 1999, and a German Application 10010616.1 filed Mar. 3, 2000.

BACKGROUND OF THE INVENTION

1. Field of the Invention

The present invention relates to monoclonal antibodies which bind specifically to the extracellular domain of the SIRP cell surface glycoproteins.

2. Related Prior Art

Signal regulator proteins (termed SIRP in that which follows) are cell surface glycoproteins which are expressed on myeloid and neuronal cells; see WO 97/48723 and Kharitonenkov et al.: A family of proteins that inhibit signalling through tyrosine kinase receptors, in Nature, volume 386, March 1997, pages 181–186.

According to the abovementioned publications, the SIRPs are involved in the negative regulation of receptor tyrosine kinase-coupled signal pathways. The SIRP family contains at least 15 members, which fall into two subfamilies. All the SIRP proteins possess an immunoglobulin-like extracellular domain, which is frequently present in receptors, and a transmembrane domain. The two subfamilies differ with regard to the presence or absence of a cytoplasmic domain which is able to bind SH-2 domains. The subfamily which is termed SIRP4 in WO 97/48723 and SIRPα in the publication by Kharitonenkov et al. possesses such a cytoplasmic domain, while the subfamily which is termed SIRP1 in WO 97/48723 and SIRPβ in the article by Kharitonenkov et al. does not possess this domain.

Cellular signal transmission is a fundamental mechanism by which external stimulations, which regulate various cellular processes, are transmitted into the interior of cells. A central biochemical mechanism in signal transmission involves the reversible phosphorylation of proteins, as a result of which the activity of mature proteins is regulated by their structure and function being altered. This process involves, on the one hand, protein phosphatases, which cleave phosphoryl groups from substrate proteins by hydrolysis which phosphoryl groups on the other hand are transferred to the substrate proteins by protein kinases. The oppositely directed functions of protein kinases and protein phosphatases regulate the signal flow in the signal transmission processes.

The protein tyrosine kinases of the receptor type constitute one group of the kinases which are involved in the reversible phosphorylation.

Tyrosine phosphatases are able to downregulate the catalytic activity of protein kinases which are involved in cell proliferation and are therefore regarded as being possible antitumour proteins. In addition to this, it is assumed that protein phosphatases are also involved in cellular differentiation processes. The best characterized member of the human SIRP family, SIRPα (or else SIRP4), is a substrate of activated receptor tyrosine kinases. Overexpression of SIRPα leads to the reaction to the receptor tyrosine kinase ligands EGF (epidermal growth factor), insulin and PDGF (platelet-derived growth factor) being reduced.

It consequently follows, from the two abovementioned documents, that SIRP acts as a negative regulator in the proliferation and differentiation of cells, which means that antibodies directed against SIRP can play a role not only when investigating the expression and function of SIRP but also in therapeutic and diagnostic applications in connection with diseases or disturbances in which there is an irregularity in a signal transmission pathway.

In this connection, WO 97/48723 describes, in a general manner, a method for producing monoclonal antibodies which are directed against SIRP polypeptides, with this publication additionally mentioning the therapeutic/diagnostic use of such antibodies, in particular in connection with immunological test methods. However, this document does not present any actual monoclonal antibodies and does not refer, in particular, to any deposition in accordance with the Budapest Treaty.

SUMMARY OF THE INVENTION

In view of the above, one object underlying the present application is to provide monoclonal antibodies which are of the abovementioned type and which bind specifically to the extracellular domain of the SIRP cell surface glycoproteins.

Monoclonal antibodies of this nature are preferably produced by hybridoma cells which are selected from the group of the following hybridoma cells which were deposited in the Deutsche Sammlung von Mikroorganismen und Zellkulturen [German Collection of Microorganisms and Cell Cultures] GmbH, DSMZ, in accordance with the Budapest Treaty, on 30.11.1999, 25.11.1999 and 13.01.2000, namely SE5A5 [DSM ACC2431], SE7C2 [DSM ACC2430], SE12B6 [DSM ACC2429], P3C4 [DSM ACC2432] (all deposited on 30.11.1999), B1D5 [DSM ACC2426] (deposited on 25.11.1999) and B4B6 [DSM ACC2443] (deposited on 13.01.2000). This assures maintenance of a viable culture of the deposit for 30 years from date of deposit. The deposit will be made available by DSMZ under the terms of the Budapest Treaty, and subject to an agreement between Applicant and DSMZ which assures permanent and unrestricted availability of the progeny of the cultures of the deposits to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14). Availability of the deposited strains is not to be construed as a license to practice the invention in contravention of the rights granted under the authority of any government in accordance with its patent laws.

The invention relates as a further object to hybridoma cells which possess the ability to produce and release such an antibody.

By means of the abovementioned antibodies SE5A5, SE7C2, SE12B6, P3C4, B1D5 and B4B6, the inventors of the present application have, for the first time, made available monoclonal antibodies, as well as hybridoma cells which produce and release these antibodies, which make it possible to selectively recognize and influence cells which exhibit the extracellular domain of SIRP. The antibodies consequently provide the physician and research worker with a versatile means, which is so far unique, for, on the one hand, detecting such cells, both in cell culture and in the body of the patient, and, on the other hand, for manipulating these cells, where appropriate, either using the antibody itself or using specific reagents which are coupled to it.

In this connection, the inventors of the present application have ascertained that the antibodies SE5A5, SE7C2, SE12B6 and P3C4 bind both to polypeptides of the SIRPα subfamily and to SIRPβ, whereas the antibodies B1D5 and B4B6 only bind specifically to SIRPβ.

In the light of this, a further object of the invention relates to a monoclonal antibody which only binds specifically to the extracellular domain of SIRPβ.

It is consequently possible to use these antibodies, in particular B1D5 and B4B6, to specifically investigate the function and expression of SIRPβ.

The inventors have furthermore ascertained that the antibodies SE5A5, SE7C2 and SE12B6 block the interaction of SIRPα with the surface marker CD47.

In the light of this, another object of the invention relates to a monoclonal antibody which binds specifically to the extracellular domain of SIRPα and blocks the interaction of SIRPα with the surface marker CD47.

The inventors have been able to demonstrate that CD47 is the extracellular ligand for human SIRP and that these two reciprocal receptors are involved in cellular adhesion which can be blocked by monoclonal antibodies SE5A5, SE7C2 and SE12B6. Consequently, these antibodies are outstandingly suitable for diagnostic and therapeutic purposes, with it being possible to achieve a very wide variety of investigations and therapeutic effects as a result of the different properties of the antibodies which have been described so far, some of which antibodies are blocking, some non-blocking, some SIRPα-specific and SIRPβ-specific and some only SIRPβ-specific.

In the light of this, yet a further object of the invention relates to a pharmaceutical composition comprising one of the novel antibodies which is preferably coupled to a cellularly directed therapeutic agent or diagnostic agent.

An antibody according to the invention which is coupled to a means for detection, for example a radioactive label, binds this means for detection indirectly to the relevant cells and thereby makes it possible to detect these cells directly, for example using X-ray diagnostic/scintigraphic methods. In a corresponding manner, coupling to a therapeutically active agent can also make it possible to exert a direct and selective effect on SIRP-carrying cells.

Within the context of the present invention, it has furthermore surprisingly been found that SIRP is not only involved in the function of myeloid cells but is likewise expressed on haematopoietic stem cells and mesenchymal cells. It has furthermore been ascertained, using the antibodies according to the invention, that various leukaemias significantly reduce the expression of SIRP on myeloid cells such that the antibodies according to the invention can be used for isolating stem cells, something which is of great interest, particularly in connection with transplanting stem cells when treating leukaemias.

In the light of this, still a further object of the present invention relates to the use of an antibody according to the invention for isolating haematopoietic stem cells.

Further advantages will be evident from the description given below.

It will be understood that the features which are mentioned above, and those which are still to be explained below, can be used not only in the combinations which are in each case specified but also in other combinations, or on their own, without departing from the scope of the present invention.

DETAILED DESCRIPTION OF PREFERRED EMBODIMENTS

The invention is explained in more detail below with the aid of application examples and implementation examples.

EXAMPLE 1

Preparing and Characterizing Monoclonal Antibodies which are Directed Against the Cell Surface Glycoprotein SIRP Recombinant fusion proteins which contain the entire extracellular domain of SIRPα1 (SIRPα1ex) or SIRPβ1 (SIRPβ1ex) are used as antigens. The sequence of the extracellular domain employed is depicted in the two above-mentioned publications.

Four to eight week-old female Balb/c mice are immunized three times, at intervals of 14 days, with 15 μg of protein which has been diluted 1:2 in RIBI adjuvant (PanSystems, Aidenbach, Germany). Four days after the last injection, the spleen was removed and fused with myeloma cells of the known strain SP2/0. The fused cells were cultured and the specific antibodies were then selected on a cell line which had been transfected with SIRPα1 or SIRPβ1.

Methods which are well known in skilled person circles were used to produce, purify and characterize the antibodies.

The reactivities and properties of the various SIRP antibodies which were prepared in this way can be taken from the attached table and the following examples.

TABLE

Reactivities and properties of SIRP antibodies

| Antibody | DSMZ ACC | Reactivity to SIRPα1 transfectants | Reactivity to SIRPβ1 transfectants | Inhibition of cell adhesion | | | Immunoprecipitation of | | | Specificity of the monoclonal antibody |
|---|---|---|---|---|---|---|---|---|---|---|
| | | | | SIRP α1ex | SIRP α2ex | SIRP β1ex | SIRP α1ex | SIRP α2ex | SIRP β1ex | |
| SE5A5 | 2431 | + | + | + | + | n.b. | + | (+) | + | α1-, (α2-), β1-specific α1, α2-blocking |
| SE7C2 | 2430 | + | + | + | − | n.b. | + | − | − | α1, (β1)-specific α1-blocking |
| SE12B6 | 2429 | + | + | − | + | n.b. | (+) | + | + | (α1-), α2-, β1-specific α2-blocking |
| P3C4 | 2432 | + | + | − | − | n.b. | + | + | + | α1-, α2-, β1-specific non-blocking |
| B1D5 | 2426 | − | + | − | − | n.b. | − | − | + | β1-specific |

TABLE-continued

Reactivities and properties of SIRP antibodies

| Antibody | DSMZ ACC | Reactivity to SIRPα1 transfectants | Reactivity to SIRPβ1 transfectants | Inhibition of cell adhesion SIRP α1ex | SIRP α2ex | SIRP β1ex | Immunoprecipitation of SIRP α1ex | SIRP α2ex | SIRP β1ex | Specificity of the monoclonal antibody |
|---|---|---|---|---|---|---|---|---|---|---|
| B4B6 | 2443 | − | + | − | − | n.b. | − | − | + | β1-specific | n.b. = no binding of cells to SIRPβ1ex with any of the haematopoietic cells which have so far been tested
(+) = weak signal Monoclonal antibodies B1D5 and B4B6 are specific for SIRPβ1. All the SIRPα1-specific monoclonal antibodies also react with SIRPβ1, which means that the antibodies SE5A5, SE7C2, SE12B6 and P3C4 can be regarded as being specific for SIRP since other members of the SIRP family possess very similar extracellular domains.

EXAMPLE 2

Expression of SIRP on Bone Marrow Cells or Peripheral Blood Cells

The monoclonal antibody P3C4 was used to investigate the surface expression of SIRP on mononuclear bone marrow cells and peripheral blood cells. By means of immunofluorescence, it was possible to demonstrate that the strongest expression is present on monocytes while there is moderate expression on granulocytes and virtually no expression on lymphocytes. CD83+ dendritic cells were likewise strongly positive with regard to SIRP.

An investigation of the coexpression of CD antigens and SIRP on various bone marrow cells showed that SIRP was expressed most strongly on C33+ and CD34+ myeloid/monocytic precursor cells. In addition to this, SIRP is also expressed on CD19+ B lymphoid cells and on immature CD117+ and AC133+ precursor cells. By contrast, no expression of SIRP was found on CD3+ T cells, CD56+ natural killer cells or glycophorin A+ erythroid precursor cells.

It follows from this that, in bone marrow, SIRP is essentially found to be expressed on myeloid and CD34+ stem cells and precursor cells.

In order to further analyse the SIRP+ subsets, CD34+ bone marrow cells were purified by means of MACS and stained with antibodies directed against CD34, SIRP and selected CD markers. It was found that SIRP is expressed on CD34+ CD90+, CD34+CD117+ and CD34+CD164$^{brigt}$ stem cells and myeloid subsets but not on CD34+CD19+ B cell subsets or CD34+CD71$^{brigt}$ erythroid precursor cells, suggesting that SIRP plays a role in the regulation of stem cell growth and differentiation.

The above results can be interpreted to the effect that SIRP is not only involved in the function of myeloid cells but also plays an important role in the regulation of stem cell differentiation.

EXAMPLE 3

Expression of SIRP on AML and CML Blasts

The antibody P3C4 was likewise employed to examine, by means of immunofluorescence, the expression of SIRP on acute myeloid leukaemia (AML) blasts and on chronic myeloid leukaemia (CML) blasts. It was found that, in contrast to normal myeloid cells, all four of the myeloid CML blast populations analysed, and 26 out of the 59 AML blast populations which were tested, were SIRP−, while 15 out of the 59 AML blasts expressed SIRP to a small degree and only 18 out of the 59 blasts expressed SIRP to the same degree as do normal myeloid or monocytic cells in bone marrow. All the immature leukaemic blasts of the M0 or M1 FAB type were SIRP− or expressed SIRP to a small extent.

These results provide evidence that SIRP expression is downregulated on many leukaemic blasts.

On the basis of the above results, it is possible that the reduced expression of SIRP in most leukaemic blasts is either the cause or a consequence of the defective proliferation of these cells.

EXAMPLE 4

Interaction of SIRP with its Extra-cellular Ligand

In order to investigate the possible interaction of SIRP with cellular components on normal and malignant haematopoietic cells, cell binding tests were carried out using immobilized fusion proteins of SIRPα1ex, SIRPα2ex and SIRPβ1ex. All the myeloblast, monoblast, erythroblast, megakaryoblast, and B lymphoblast and T lymphoblast cell lines which were tested bound strongly to SIRPα1ex and SIRPα2ex but not to SIRPβ1ex, with dilution series demonstrating that B lymphoblast and T lymphoblast cell lines possess a larger number of binding sites for SIRP.

It was furthermore possible to demonstrate that some of the monoclonal antibodies according to the invention inhibit the binding of cells to SIRPα1ex and SIRPα2ex, as is shown in the table from Example 1.

Further investigations of the expression of possible SIRP ligands showed that soluble SIRPα1ex and SIRPα2ex bound strongly to lymphocytes, while their binding to monocytes and granulocytes was substantially weaker.

In order to identify the extracellular ligand for SIRPα1 and SIRPα2 on haematopoietic cells, the SIRP-negative, but strongly SIRPα1ex-binding and SIRPα2ex-binding, CCRF-CEM cells were used to produce monoclonal antibodies which inhibit the binding of SIRPα1ex and SIRPα2ex to these cells. The antibody CC2C6, which was found in this context, blocked this binding completely.

The cellular reactivity of this antibody was compared with that of 166 different antibodies directed against CD molecules, in connection with which it emerged that CC2C6 recognizes CD47 as being the extracellular ligand for SIRPα1 and SIRPα2.

It was furthermore found that only functionally active, CD47-specific monoclonal antibodies are able to block the interaction between CD47 and SIRP completely, while non-functional monoclonal antibodies have no effect on this interaction. This suggests that the binding of SIRP to CD47 is essential for many of the functions described for CD47. In the light of this, both the blocking and the non-blocking antibodies according to the invention are valuable tools for investigating the participation of SIRP in various immunological processes in vitro.

What is claimed is:

1. A monoclonal antibody produced by hybridoma cells, wherein said hybridoma cells are selected from the group consisting of the hybridoma cells deposited with Deutsche Sammlung für Mikroorganismen und Zellkulturen GmbH, DSMZ as DSM ACC2431, DSM ACC2430, DSM ACC2429, DSM ACC2432, DSM ACC2426 and DSM ACC2443.

2. A hybridoma cell line selected from the group consisting of DSM ACC2431, DSM ACC2430, DSM ACC2429, DSM ACC2432, DSM ACC2426 and DSM ACC2443, all deposited with Deutsche Sammlung für Mikroorganismen und Zellkulturen GmbH, DSMZ.

3. A composition, comprising the antibody of claim 1.

4. A method for detecting signal regulator protein (SIRP)-expressing cells, comprising the step of contacting a sample supposed to contain such cells with the antibody of claim 1 and detecting specific binding of the antibody to cells in the sample.

* * * * *